United States Patent [19]

Hoover

[11] Patent Number: 4,904,240
[45] Date of Patent: Feb. 27, 1990

[54] METHOD AND APPARATUS FOR STARTING INTRAVENOUS SOLUTIONS

[76] Inventor: Rocklin L. Hoover, Route 3, Box 314X-4, Sumter, S.C. 29154

[21] Appl. No.: 204,246

[22] Filed: Jun. 9, 1988

[51] Int. Cl.⁴ .............................................. A61M 5/00
[52] U.S. Cl. ...................................... 604/53; 604/167; 604/168
[58] Field of Search ................. 604/167, 164, 168, 52, 604/53

[56] References Cited

U.S. PATENT DOCUMENTS

| | | | |
|---|---|---|---|
| 4,108,175 | 8/1978 | Orton | 604/168 |
| 4,269,186 | 5/1981 | Loveless et al. | 604/168 |
| 4,317,445 | 3/1982 | Robinson | 604/168 |
| 4,338,934 | 7/1982 | Spademan | 604/167 |
| 4,772,264 | 9/1988 | Cragg | 604/168 |

*Primary Examiner*—Stephen C. Pellegrino
*Attorney, Agent, or Firm*—Cort Flint

[57] ABSTRACT

A method and apparatus for starting and feeding intravenous solutions through a catheter is disclosed comprising two chambers in tandem, the first chamber having a catheter attached to one end, a resealing port opposite the catheter and a permanent tube port for receiving intravenous solutions into the first chamber, and the second chamber, or flash chamber, having a long hollow needle at one end, inserted through the resealing port and catheter of the first chamber, and a squeeze bulb at the other end for urging a sample of blood through the needle into the flash chamber to signal that a blood vessel has been penetrated. To place the catheter in a blood vessel, the intravenous solution is connected to the tube port of the first chamber, the bulb is squeezed, then the needle carrying the catheter is pushed into the skin and the squeezed bulb released. Blood flashes into the flash chamber, urged by the vacuum created by the released squeeze bulb, as the needle enters a blood vessel. Then the catheter is pushed forward into the blood vessel as the flash chamber is held in place so that the needle backs in sequence through the chamber, the first chamber and the resealing port. The needle, flash chamber with bulb and blood sample, are then discarded in an appropriate receptacle. The intravenous solution is turned on at the appropriate rate and the apparatus is secured in place.

7 Claims, 2 Drawing Sheets

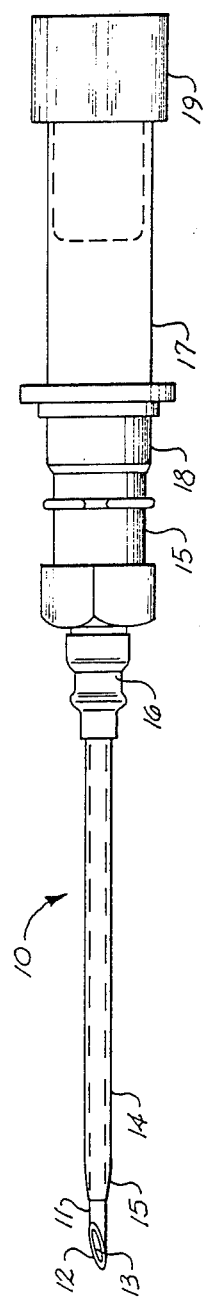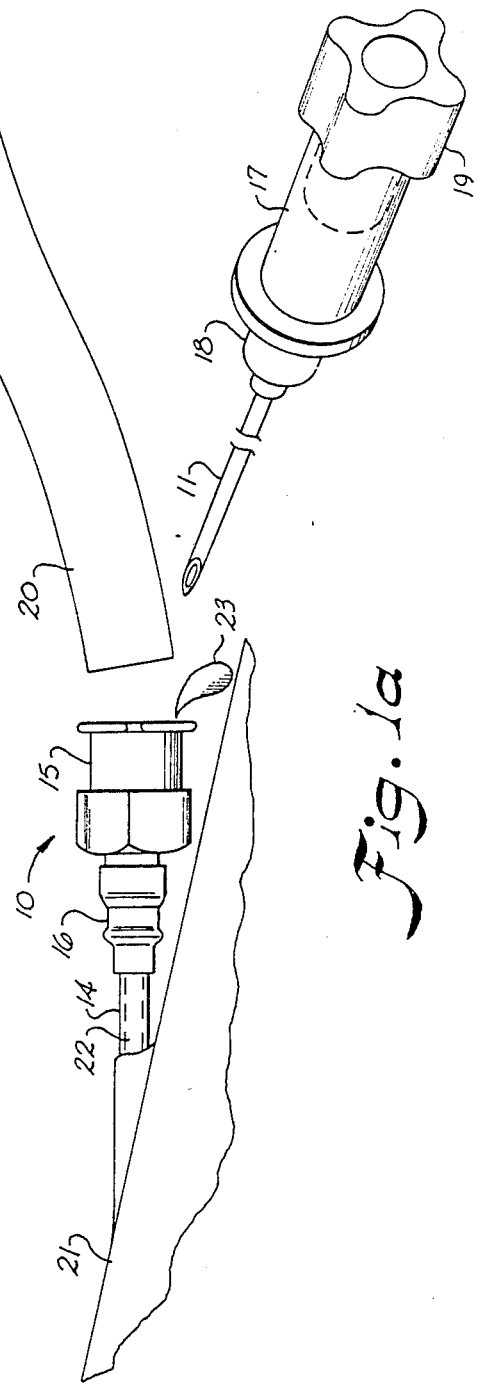

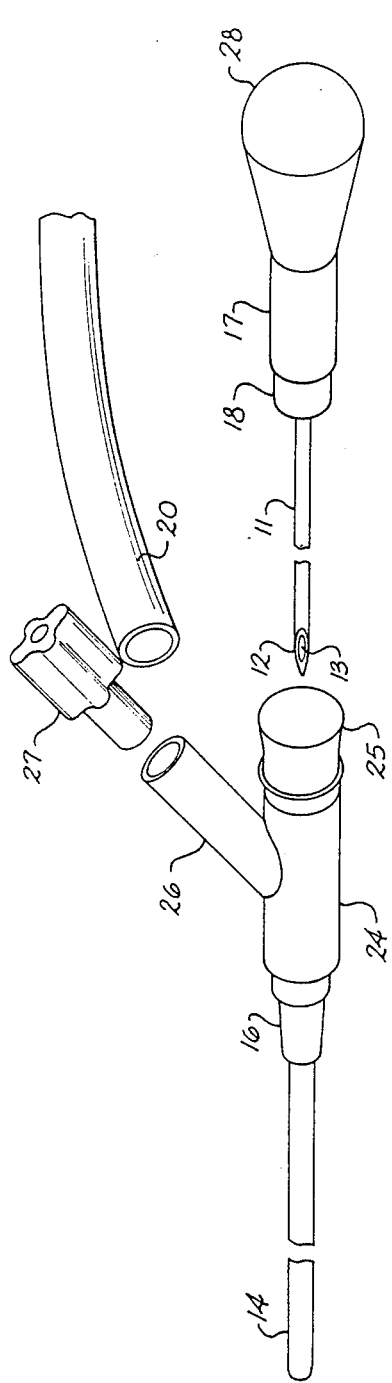
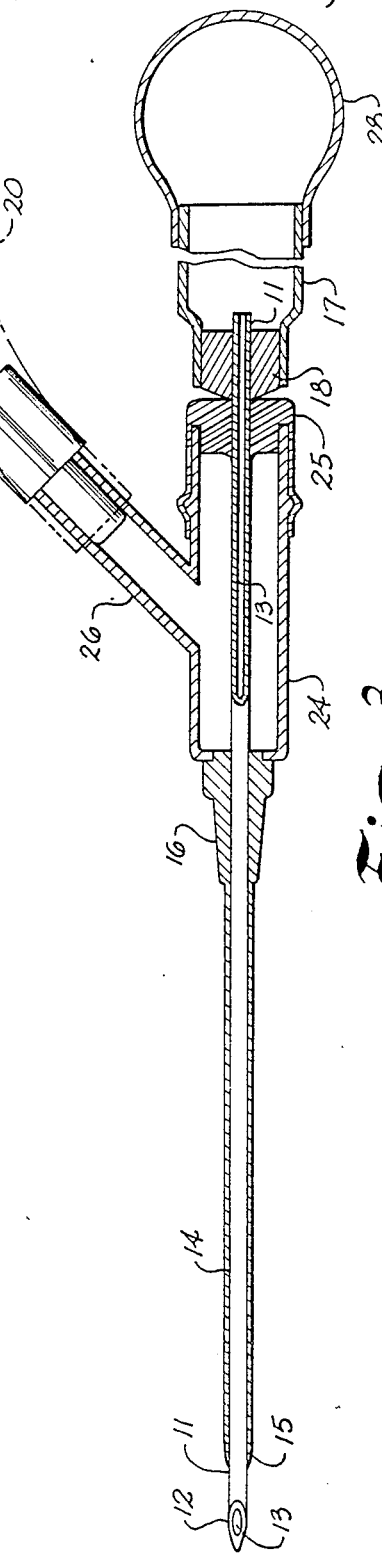

METHOD AND APPARATUS FOR STARTING INTRAVENOUS SOLUTIONS

BACKGROUND OF THE INVENTION

The present invention relates to catheter placement apparatuses and methods for use. More specifically, the present invention is a method and improved, closed catheter placement apparatus for starting and feeding intravenous solutions without spillage of blood.

Starting and feeding intravenous solutions is a common hospital procedure Numerous intravenous solutions, including glucose in water, saline and glucose in water, and others, sometimes with specific medications or anesthetics, are introduced into the bodies of patients. The catheter placement procedure employs standard catheter placement units which comprise a needle, a flash chamber attached to the needle, and a catheter surrounding and carried by the needle attached to a universal base. (FIGS. 1 and 1a, more fully described below depict the prior art catheter placement apparatus.) The needle is hollow; its tip, bevelled, for ease in penetration of the skin. The base has an end plug that is not air tight. As the bevelled tip of the hollow needle enters the blood vessel, blood courses through the flash chamber displacing air from the chamber passed the end plug.

The blood in the flash chamber signals the medical attendant that a blood vessel has been entered.

The catheter is then gently pushed into the blood vessel as the hollow needle is withdrawn from within the catheter and the universal base. At that point there is an open path from the blood vessel, through the hollow catheter to the universal base. As quickly as possible, the medical attendant connects an administration fluid set carrying the intravenous solution into the base. Usually a small quantity of blood escapes from the base when the needle is withdrawn and before the connection of the tube carrying the intravenous solution can be accomplished.

With the increased use of gloves by medical attendants for all invasive hospital procedures, dexterity is lessened and more blood spilled in the course of administering intravenous solutions. Spilled blood may expose medical personnel to contamination and is therefore to be avoided. Especially with the possibility that the patient may have Acquired Immunodeficiency Syndrome, or AIDS, avoiding contaminated blood is of great importance to medical personnel.

It is an object of the present invention to provide a closed system method and apparatus for the starting and feeding of intravenous fluids. It is a further object of the present invention to start intravenous solutions easily and quickly. It is an object of the invention to enable the starting of intravenous solutions without blood spillage. It is an object of the present invention to reduce exposure of hospital personnel to contamination from the blood of the patient. It is a further object of the present invention to be inexpensive to manufacture.

SUMMARY OF THE INVENTION

The above objectives are accomplished according to the present invention by a method and apparatus having a catheter placement unit having two chambers in tandem. A first chamber is in communication with a catheter, and a second, or flash chamber is in communication with a long hollow needle. The needle slidably carries the catheter, positioned outside and coaxially with the needle, into the body of the patient. The first chamber has a first, permanent tube port for receiving the intravenous solution from an administration set which can be attached and primed prior to accomplishing the blood vessel puncture, and a second, resealing port on the end of the first chamber opposite the catheter. A squeeze bulb is attached to the flash chamber. The long hollow needle traverses the resealing port, the interior of the first chamber and the catheter. The squeeze bulb of the present invention is squeezed to evacuate air from the flash chamber, the needle carrying the catheter then enters the body and the squeeze bulb is released. When the tip of the needle enters a blood vessel, a small quantity of blood flows through the hollow needle to the flash chamber, urged by the vacuum created upon release of the squeeze bulb. Next, the catheter is gently slid forward into the blood vessel as the needle and flash chamber with squeeze bulb are withdrawn in sequence from the catheter, the first chamber and the resealing port. The intravenous solution is turned on and allowed to flow into the patient through the previously connected administration set without any blood spillage or contamination. The resealing port can be reused for the administration of medications if so desired at later times.

DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein:

FIG. 1 shows an example of the prior art catheter placement unit for starting intravenous solutions;

FIG. 1a shows an example of the prior art after the needle has been withdrawn and before the tube carrying intravenous fluid is attached to the universal base. FIG. 1a also shows a drop of blood issuing from the universal base;

FIG. 2 shows an exploded perspective view of the present invention; and

FIG. 3 shows a cross sectional side view of the present invention.

DESCRIPTION OF A PREFERRED EMBODIMENT

The present invention is a method and an improved, closed apparatus for starting and feeding intravenous solutions in a portion of a human body.

As best shown in FIG. 1, the prior art unit 10 comprises a long hollow needle 11 having a bevelled tip 12, and interior 13. The needle is typically made of metal and the needle 11 comes in a variety of lengths and diameters for different medical intravenous uses. A catheter 14 surrounds coaxially the hollow needle 11. Needle 11 slides freely within catheter 14. Tip 15 of catheter 14 is tapered slightly so that catheter 14 enters the body more easily. Catheter 14 is a flexible, hollow tube for holding open a passage through the skin, tissues and blood vessel wall of the portion of the body to receive the intravenous solution. Catheter 14 is attached to a universal base 15 by first sealing collar 16. Attached to hollow needle 11 is flash chamber 17 sealed to hollow needle 11 by a second collar 18 that mates with universal base 15 when hollow needle is fully inserted within catheter 14. An end plug 19 closes chamber 17. Chamber 17 is made of a translucent or clear plastic so that blood entering the chamber can be seen by the user of the prior art unit 10. As best shown in FIG. 1a, use of the prior art catheter placement unit 10 spills blood 23. After hollow needle 11 carries catheter 14 into a body 21, a small amount of the blood will enter flash chamber 17 which is in communication with hollow needle 11. Interior 13 of hollow needle 11 from tip 12 through to flash chamber 17 defines a passage for blood, under venous pressure, to evacuate air within flash chamber 17 through end plug 19. Medical personnel then know that a blood vessel wall has been penetrated and withdraw hollow needle 11 and flash chamber 17 as catheter 14 is gently pushed forward into the blood vessel. When hollow needle 11 has cleared universal base 15, a tube 20 leading to the intravenous solution is quickly attached to universal base 15 but usually not without spillage of blood.

Referring now in more detail to the invention, FIG. 2 shows an exploded view of the present invention wherein catheter 14 is attached to a first chamber 24 by a sealing collar 16. Opposite sealing collar 16 is a resealable port 25 made of a rubberized material of suitable thickness which reseals automatically upon needle withdrawal. Resealing port 25 should be sufficiently thick and resilient so that, as tip 12 of hollow needle 11 passes out of resealing port 25, a passage formed by hollow needle 11 closes to form a blood-tight seal before tip 12 clears resealing port 25. First chamber 24 has a permanent tube port 26 for receiving intravenous fluid from tube 20. Permanent port 26 has a temporary end plug 27 to keep the interior of first chamber 24 sterile. Hollow needle 11 having bevelled tip 12 open to the interior 13 of hollow needle 11 is attached to the flash chamber 17 by second collar 18. Opposite hollow needle 11 is a squeeze bulb 28.

The detailed relationship of the elements of the present invention is best seen in FIG. 3. The squeeze bulb 28 closes flash chamber 17 opposite hollow needle 11. The interiors of squeeze bulb 28, flash chamber 17 and hollow needle 11 form a continuous passage for receiving a small quantity of blood when tip 12 of hollow needle 11 penetrates a blood vessel wall. By squeezing bulb 28 before tip 12 is introduced into the body, air within the flash chamber is evacuated from tip 12 of hollow needle 11. After tip 12 of hollow needle 11 enters the body, squeeze bulb 28 may be released. A vacuum thus created within flash chamber 17 should not be so great as to attach tissue to tip 12, but should be sufficient to urge blood from a blood vessel, when penetrated, to enter flash chamber 17 thus signalling to medical personnel that a blood vessel wall has been penetrated.

Tube 20 is attached to permanent port 26 in place of end plug 27 prior to initiation of procedure to form closed system or tube 20 may be attached to permanent port 26 at any time before hollow needle 11 is withdrawn, preferably before the blood vessel wall has been penetrated. Hollow needle 11, flash chamber 17 and bulb 28 are withdrawn as catheter 14 is gently slid forward into the blood vessel. Resealing port 25 seals as hollow needle 11 is withdrawn. Port 26 is preferably positioned to the side of the first chamber so as not to interfere with hollow needle 11. It is important in the present invention that permanent port 26 be configured at the smallest angle with respect to the axis of the needle 11 so as to minimize lateral forces on the body caused by the weight of tube 20. Alternatively to the orientation shown in FIG. 3 would be an expansion of first chamber to permit the axes of tube 20 and needle 11 to be placed in parallel.

While a preferred embodiment of the invention has been described using specific terms, such description is for illustrative purposes only, and it is to be understood that changes and variations may be made without departing from the spirit or scope of the following claims.

What is claimed is:

1. A catheter placement apparatus for starting and feeding intravenous solutions from an administrative tube set into a blood vessel of a human body comprising:

a first chamber having a first interior;

a permanent tube port carried on said first chamber in fluid communication with said first interior for receiving intravenous solutions from said tube set and delivering said solutions into said first interior upon connection of said tube and said permanent port;

a catheter carried by said first chamber having a second interior in fluid communication with said first interior so that said intravenous solutions can flow from said first interior of said first chamber into said second interior of said catheter;

a resealable port carried by said first chamber opposite said catheter;

a hollow needle having a third interior, said hollow needle having a beveled tip at a first end for penetrating said body, and said hollow needle having a second end opposite said tip;

said hollow needle being slidably positioned within said catheter and traveling said first chamber through said resealable port, said tip of said hollow needle being outside said catheter and said second end of said hollow needle being outside said resealable port so that said third interior is isolated from said first and second interiors; and indicator means for signaling that said hollow needle has penetrated said blood vessel in said body which includes a transparent flash chamber having one end carried by said hollow needle in tandem with said first chamber, a squeeze bulb carried by an opposite end of said flash chamber in tandem with said flash chamber which creates a vacuum in said hollow needle and flash chamber upon being squeezed and released for urging blood into said flash chamber, and said flash chamber and squeeze bulb being carried coaxially and sequentially in tandem with said hollow needle so that said flash chamber is unobstructed for detecting blood in said flash chamber upon vein puncture.

2. The apparatus of claim 1 wherein said squeeze bulb is constructed and arranged to draw a vacuum which pulls a small sample of blood from said blood vessel penetrated by said needle tip but not draw a sufficient vacuum to adhere body tissues to said needle tip.

3. The apparatus of claim 1 wherein said resealable port comprises a plug of resilient material carried by an open end of said first chamber having a sufficient thickness so that a passage made by said needle in said resilient material closes blood-tight as the tip of said needle is pulled outwardly through said resealable port.

4. The apparatus of claim 1 wherein an axis of said permanent tube port projecting from said first chamber and an axis of said catheter are arranged at a minimal angle with respect to each other so the lateral forces produced by said tube on said catheter are reduced.

5. The apparatus of claim 4 wherein said permanent tube port has a temporary end plug so that said interior of said first chamber may be kept sterile.

6. A bloodless method for starting and feeding intravenous solutions from an administrative tube set using an apparatus having a first chamber with a catheter extending from one end and a releasably port opposite said catheter, said first chamber having a permanent port for receiving intravenous solutions from said tube set into said first chamber; a flash chamber having a squeeze bulb at one end and a hollow needle projecting from an other end which traverses said resealing port, said first chamber, and said catheter of said first chamber, said catheter and said hollow needle being coaxial and said needle carrying said catheter, which method comprises the steps of:

squeezing said squeeze bulb;

introducing said hollow needle into a portion of a body having a vein;

releasing said squeeze bulb to create a slight vacuum in said hollow needle;

penetrating said vein whereupon blood from said vein urged by said vacuum enters said flash chamber through said hollow needle signaling said vein has been penetrated;

attaching said tube to said permanent port; and pushing said catheter gently into the vein while withdrawing said hollow needle through said catheter, said first chamber and said resealing port to close off said first chamber;

whereby penetration of said catheter into said blood vessel is detected by visually inspecting said flash chamber while said hollow needle and flash chamber are subsequently removed from said first chamber through said resealing port so that no blood spillage occurs externally of said first chamber or contacts the skin of said attendant.

7. The method of claim 6 wherein attachment of said tube to said permanent port occurs before the step of penetrating a blood vessel to assure a closed system apparatus.

* * * * *